United States Patent
Dall'Asta et al.

(10) Patent No.: US 6,888,010 B2
(45) Date of Patent: May 3, 2005

(54) PROCESS FOR THE PREPARATION OF 5-FORMYLPHTHALIDE

(75) Inventors: Leone Dall'Asta, Milan (IT); Giovanni Cotticelli, Cernusco sul Naviglio (IT)

(73) Assignee: Infosint SA, Cantoni dei Grigioni (CH)

( * ) Notice: Subject to any disclaimer, the term of this patent is extended or adjusted under 35 U.S.C. 154(b) by 0 days.

(21) Appl. No.: 10/776,626

(22) Filed: Jan. 31, 2004

(65) Prior Publication Data

US 2004/0225136 A1 Nov. 11, 2004

Related U.S. Application Data

(63) Continuation of application No. PCT/EP02/08551, filed on Jul. 29, 2002.

(30) Foreign Application Priority Data

Aug. 2, 2001 (EP) .............................. 01830518

(51) Int. Cl.$^7$ .............................................. C07D 307/88
(52) U.S. Cl. ......................................................... 549/307
(58) Field of Search ......................................... 549/307

(56) References Cited

FOREIGN PATENT DOCUMENTS

WO           02/48133 A2  *  6/2002

* cited by examiner

*Primary Examiner*—Taofiq Solola
(74) *Attorney, Agent, or Firm*—Katten Muchin Zavis Rosenman

(57) ABSTRACT

There is described a process for the preparation of 5-formylphthalide by hydrogenation of a halide of 5-carboxyphthalide, dissolved in a dipolar aprotic solvent, in the presence of a catalyst. Furthermore, the use of 5-formylphthalide in the preparation of citalopram is described.

10 Claims, No Drawings

PROCESS FOR THE PREPARATION OF 5-FORMYLPHTHALIDE

CROSS-REFERENCE TO RELATED APPLICATION

The present application is a continuation of International Application No. PCT/P02/08551 which was filed on Jul 29, 2002.

The present invention concerns a process for the preparation of 5-formylphthalide or 1-oxo-1,3-dihydro-5-isobenzofurancarbaldehyde by hydrogenation of a halide of 5-carboxyphthalide.

The 5-formylphthalide is a known compound of formula

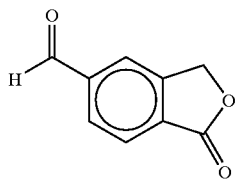

(I)

used as an intermediate in various processes of synthesis.

For example, in the European patent application entitled "Process for the preparation of 5-substituted isobenzofurans", concurrently filed in the name of the same applicant and incorporated herein by reference, 5-formylphthalide is employed as starting material in the synthesis of 1-[3-(dimethylamino)propyl]-1-(4-fluorophenyl)-1,3-dihydro-5isobenzofurancarbonitril, represented by formula

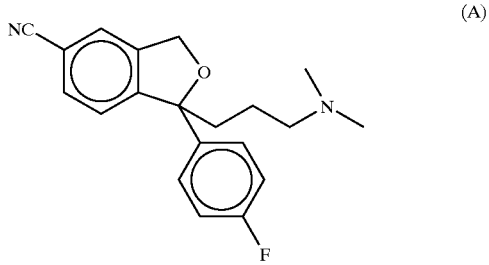

(A)

an active substance known under its International Non-proprietary Name "citalopram", used in form of its hydrobromide for the preparation of pharmaceutical compositions indicated for the treatment of depression.

In particular, such an application discloses a process for the preparation of citalopram consisting of treating 5-formylphthalide with a O-substituted hydroxylamine, submitting the O-substituted oxime thus obtained, stable in the conditions of a Grignard reaction, to two subsequent Grignard reactions, one with a 4-fluorophenylmagnesium halide and the other, on the product thus obtained, with a [3-(dimethylamino)propyl]magnesium halide.

The O-substituted 3-hydroxymethyl-4-[α-hydroxy-α-3-(dimethylamino)propyl-4-fluorobenzyl]benzaldoxine thus prepared is cyclized, the corresponding O-substituted 1-[3-(dimethylamino)propyl]-1-(4-fluorophenyl)-1,3-dihydro-5-isobenzofurancarbaldoxime is O-deprotected and the 1-[3-(dimethylamino)propyl]-1-(4-fluorophenyl)-1,3-dihydro-5-isobenzofurancarbaldoxime thus obtained is finally transformed into citalopram. Alternatively, the 1-[3-(dimethylamino)propyl]-1-(4-fluorophenyl)-1,3-dihydro-5-isobenzofurancarbaldoxime, O-substituted with a diphenylmethyl or triphenylmethyl group, can be concurrently deprotected and converted into citalopram in only one step, by treatment for example with formic-acetic anhydride.

The only method disclosed in the literature, for the preparation of 5-formylphthalide is that described in J. Chem. Soc. (1925), 127, 2275–2297, whereby the 5-formylphthalide is obtained, in admixture with 2,4-diformylbenzoic acid, by chlorination of 2,4-dimethylbenzoyl chloride and treatment of the resulting mixture with chalk in water. This synthesis, however, does not allow the desired product to be obtained in satisfactory yields. A further disadvantage is represented by the difficulties in isolating the desired product from the complex reaction mixture.

Literature discloses various, generally applicable methods for the preparation of aldehydes and, in particular, various reduction methods such as Rosenmund reaction [Encyclopaedia of Organic Reagents for Organic Synthesis, vol. 6, pages 3861–3865, J. Wiley & Sons (1995)]. Such a reaction involves the hydrogenation of acyl halides, preferably chlorides, dissolved in apolar aromatic solvents such as benzene, toluene or xylene or in ethers such as tetrahydrofuran or dioxane, in the presence of partially inactivated catalytic systems. Inactivation of the catalyst, made for example by addition of solutions of sulphur dissolved in quinoline or thiourea, is necessary in order to avoid the further reduction of the aldehyde function to primary alcohol. However, such classic method cannot be used for the industrial preparation of 5-formylphthalide. In fact, owing to the partial precipitation of the product and of the consequent inactivation of the catalyst which occurs under the classic conditions of Rosenmund, the reaction proceeds more and more slowly, until to its stopping, before it is completed. In order to bring the conversion yields to acceptable levels, it becomes therefore necessary to make repeated additions of fresh catalyst, with consequent increase of costs and greater difficulties in isolating and wasting the exhausted catalyst Furthermore, the hydrogenation carried out in apolar aromatic solvents or in ethers, notwithstanding the partial inactivation of the catalyst, gives rise to the formation of significant amounts of alcohol which, beside reducing the yields in desired product, complicates its purification.

Finally, the formation of a precipitate in the presence of a supported catalyst renders the final working of the reaction mixture and the recovery of 5-formylphthalide particularly difficult.

We have now found a new, particularly simple process for preparing 5-formylphthalide of high purity in good yields, which, in respect of the classical reaction of Rosenmund, not only solves the above mentioned drawbacks of poor conversion, of alcohol formation and of difficult working up, but also makes it possible to avoid the inactivation of the catalyst and the use of additional basic compounds.

Thus the present invention provides a process for the preparation of 5-formylphthalide of formula

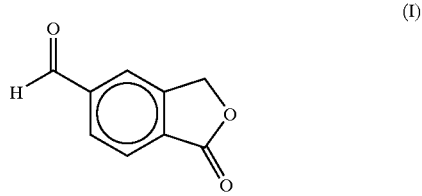

(I)

which comprises submitting a halide of formula

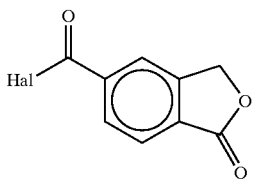

(II)

wherein Hal represents chlorine, bromine or iodine, dissolved in a dipolar aprotic solvent, to hydrogenation The halide of formula II, in its turn, can be obtained by treatment of 5-carboxyphthalide or of an alkaline salt thereof, with a phosphor or sulphur halide such as phosphorus pentachloride, phosphorus trichloride, phosphor tribromide, phosphoryl chloride, sulphuryl chloride or, preferably, thionyl chloride, in an organic solvent.

A particularly preferred halide of formula II is the chloride which can be prepared, for example, as described in J. Chem. Soc, (1931), 867–871.

The 5-carboxyphthalide starting material is known from the literature (U.S. Pat. No. 3,607,884—DE 2.630.097) and can be easily prepared in very good yields for example as described in Italian patent application MI2000A000050.

Practically, it is preferable to treat 5-carboxyphthalide, optionally dissolved in an organic solvent, with thionyl chloride in the presence of catalytic amounts of N,N-dimethyl formamide, heating until the development of hydrogen chloride is no longer observed. Then, the chloride of formula II is preferably isolated and used in the present process.

According to the present invention, the halide of formula II, preferably the 5-chlorocarbonylphtalide, dissolved in a dipolar aprotic solvent, selected among N,N-dimethyl formamide, dimethylsulfoxide, acetonitrile or, preferably, N,N-dimethylacetamide, is hydrogenated in the presence of a hydrogenation catalyst, preferably of palladium on a support. As a suitable support, charcoal or barium sulphate are preferably used.

Hydrogenation can be carried out at ambient pressure or under pressure, practically at a pressure of from 1 to 5 bar, preferably between 2.5 and 3.5 bar. The reaction temperature may generally vary from room temperature to 120° C., advantageously between 40 and 80° C., preferably it is of about 60° C.

The concentration of the halide of formula II is generally comprised between 50 and 90 g/l, preferably between 60 and 80 g/l. Advantageously, it is of about 70 g/l.

The supported catalyst is generally used in a weight by weight (w:w) ratio, in respect of the halide of formula II, comprised between 0.4:1 and 0.01:1, advantageously between 0.2:1 and 0.05:1, preferably of about 0.1:1.

After removal of the catalyst, 5-formylphthalide (I) is isolated according to the known techniques, for example by evaporating the solvent, taking up the residue with a suitable solvent and crystallizing, or by diluting the reaction mixture with a suitable solvent and recovering the precipitated product.

According to the process of the present invention, 5-formylphthalide (I) is prepared in a sufficiently pure state for its use as intermediate, and in satisfactory global yields, generally higher than 60%.

According to its preferential aspect, the present invention provides a process for the preparation of the 5-formylphthalide (I) which comprises submitting the 5-chlorocarbonyl phthalide, dissolved in N,N-dimethylacetamide, to hydrogenation in the presence of 5% Pd/BaSO$_4$ the catalyst:5-chlorocarbonylphthalide (w:w) ratio being of about 0.1:1, at a pressure of 3 bar and at a temperature of 60° C.

The isolation conditions are those illustrated hereinabove.

The following examples illustrate the invention without, however, limiting it.

$^1$H-NMR spectra have been registered by a Varian 300 Mz spectrometer in DMSO-d$_6$ or CDCl$_3$.

EXAMPLE 1

(a) 5-Chlorocarbonylphthalide

To a mixture of 1800 ml of thionyl chloride and 8.1 ml of N,N-dimethylformamide, 750 g (4.21 moles) of 5-carboxyphthalide are added under stirring. The mixture is heated slowly to reach an inner temperature of 60° C. in one hour, then it is kept at this temperature for another hour and finally it is brought to the reflux. After refluxing for 6 hours, about 600 ml of thionyl chloride are distilled off at a temperature of 80÷85° C., by replacing them by addition of toluene. Distillation is continued for a total of 2800 ml with concurrent replacement of the solvent by addition of 3800 ml of toluene. The mixture is slowly cooled and, at 80° C., the crystallization of the product begins. Cool to 10÷15° C. by continuing stirring for 15 hours. The hygroscopic product is filtered, washing with a total of 1500 ml of toluene, then it is dried under vacuum at 55° C. to give 710 g (86%) of 5-chlorocarbonylphthalide with a purity of 99% (HPLC).

(b) 5-Formylphthalide: Hydrogenation in N,N-dimethylacetamide

In a hydrogenator, 23 l of N,N-dimethylacetamide, 1.65 Kg (8.39 moles) of 5-chlorocarbonylphthalide and 200 g of 5% Pd/BaSO$_4$ are charged, then hydrogen is charged at 3 bar thereinto and the mixture is heated at 60÷3° C. for a total of 48 hours. The mixture is cooled and, after removal of the catalyst by filtration, concentrated under vacuum at 75° C. to a solid residue. The product is treated with 8 l of deionized water and, at 5÷10° C. under stirring, the pH of the mixture is adjusted to 7.0÷7.5 by addition of 2.3 l of 10% ammonium hydroxide solution. After a 30-minute stirring, the product is filtered, washed with deionized water and dried under vacuum at 50° C. to give 885 g (65%) of desired product having m.p.=163÷165° C. (in J. Chem. Soc. 1925, page 2290 a m.p.=159÷160° C. is given).

$^1$H-NMR (DMSO-d$_6$) δ ppm: 5.51 (s, 2H, CH$_2$O), 8.00÷8.12 (m, 2H, arom.), 8.18 (s, 1H, arom.), 10.17 (s, 1H, CHO).

EXAMPLE 2

5-Formylphthalide: Hydrogenation in N,N-dimethylacetamide

To a solution of 8.58 g (0.043 mole) of 5-chlorocarbonylphthalide in 120 ml of N,N-dimethylacetamide in a hydrogenator 1 g of 5% Pd/BaSO$_4$ is added and hydrogen at 2.5 bar is charged thereinto. The mixture is heated to 60° C., kept at this temperature for 40 hours at 2.5÷3 bar, then cooled, filtered to remove the catalyst and concentrated under vacuum at 75° C. The residue is taken up with 50 ml of deionized water, then the suspension is neutralized with 10% ammonium hydroxide solution to a pH=7.5 and the product is filtered to give 4.4 g (63%) of 5-formylphthalide with m.p.=162÷163° C.

The mixture quinoline-sulfur used to partially inactivate the catalyst in the following comparative examples has been prepared according to Org. SynthColl. 3, 627.

EXAMPLE 3

Comparative Example

Hydrogenation in Toluene

In a hydrogenator a mixture of 7 g (0.036 mole) of 5-chlorocarbonylphthalide, 50 ml of toluene, 0.1 ml of the quinoline/sulfur mixture and 0.7 g of previously reduced 5% Pd/BaSO$_4$ is charged. The mixture is hydrogenated at 80° C. under 3.5 bar for 7 hours. At this point the reaction no longer proceeds because of the co-precipitation of the formed product Thus, it is stopped and the mixture is filtered in the warm in order to put the product. into solution again. A second amount of 0.7 g of 5% Pd/BaSO$_4$ is added to the filtrate and the hydrogenation starts again under the above described conditions. After 15 minutes, no more absorption of hydrogen is observed. Hydrogenation is stopped and the catalyst is filtered off in the warm. After cooling, the solution is concentrated under vacuum to a residue which is taken up with ethyl acetate. The organic phase is washed with a 5% aqueous solution of NaHCO$_3$, concentrated to a little volume and the separated product is filter. There is obtained 4.2 g of 5-formylphthalide with a purity (HPLC)=42% (yield 30%).

EXAMPLE 4

Comparative Example

Hydrogenation in Tetrahydrofuran

A mixture of 7 g (0.036 mole) of 5-chlorocarbonylphthalide, 50 ml of tetrahydrofuran, 0.1 ml of the quinoline/sulfur mixture and 1 g of 10% Pd/C is hydrogenated at 3.5 bar and 35÷40° C. for 3 hours. After 3 hours a stoppage of the hydrogen absorption is observed. Thus, the mixture is cooled, diluted with dichloromethane, filtered, and by a HPLC control the presence of equivalent amounts of alcohol and aldehyde is observed. The mixture is concentrated under vacuum and the residue is taken up with ethyl acetate. The crystalline product is filtered and dried to obtain 4 g of 5-formylphthalide with a purity (HPLC)=44% (yield 30%).

EXAMPLE 5

Comparative Example

Hydrogenation in Dioxane

In a hydrogenator, 8.2 g (0.042 mole) of 5-chlorocarbonylphthalide, 50 ml of dioxane and 0.77 g of 5% Pd/BaSO$_4$ are charged and the mixture is hydrogenated at 4 bar and 70° C. for 7 hours. After this period of time, the reaction no longer proceeds because of the co-precipitation of the formed product; thus, the hydrogenation is stopped, the mixture is diluted with 120 ml of tetrahydrofuran and stirred at 40° C. for 20 minutes. The solid is filtered off and the solution is concentrated to a little volume. The crystalline product is recovered by filtration and dried to give 3.3 g of 5-formylphthalide with a purity (HPLC)=82% (yield 40%).

EXAMPLE 6

Use of 5-Formylphthalide for the Preparation of Citalopram Hydrobromide (a) To a suspension of 35 g (0.216 mole) of 5-formylphthalide in 800 ml of dichloromethane, 800 ml of a solution of 65.4 g of triphenylmethoxyamine (0.25 mole) in 350 ml of dichloromethane are added in 45 minutes. After about 2 hours at 25±27° C., the obtained solution is concentrated under vacuum to a volume of about 100 ml, whereby the crystallization of the product begins. A volume of 200 ml of methanol is added to the mixture, which is concentrated again to a little volume, then it is diluted with further 300 ml of methanol and let to stand at 20±25° C. for 2 hours to complete the crystallization. A further volume of 700 ml of methanol is added to the thick suspension, the mixture is stirred at 20±25° C. for one hour, the product is filtered, washed with 100 ml of methanol and dried under vacuum at 40° C. to give 75.2 g of O-triphenylmethyl-2-oxo-1,3-dihydro-5-isobenzofurancarbaldoxime with m.p.=203÷206° C. and purity (HPLC)=95.1%. From the mother liquors, by concentration to a little volume, further 10.9 g of product having a purity of 98.2% are recovered. Total yield: 86.1 g (90%).

$^1$H-NMR (CDCl$_3$) δ ppm: 5.23 (s, 2H, CH$_2$O), 7.22÷7.40 (m, 15H, arom., triphenylmethyl), 7.58 (m, 1H, arom., phthalide), 7.83 (d, 1H, arom., phthalide), 8.38 (s, 1H, CH=N).

(b) To a solution of 25 g (0.06 mole) of O-triphenylmethyl-2-oxo-1,3-dihydro-5-isobenzo furancarbaldoxime in 125 ml of tetrahydrofuran, 92.8 ml of a 14.5% solution of 4-fluorophenylmagnesium bromide in tetrahydrofuran are slowly added in 3 hours and a half, at 15° C. and under nitrogen atmosphere. After a control by HPLC to verity that the unreacted starting material is lower than 2% (area), the mixture is slowly cooled to 10° C., then 65 ml of a 30% solution of [3-dimethylamino)propyl]magnesium chloride in tetrahydrofuran are slowly added at 5÷10° C. thereinto. After a HPLC control showing that the content in diol is of 23.1 g, 1400 g of a 15% aqueous solution of ammonium chloride is added at 5÷10° C. to the mixture under stirring. Said mixture is stirred for 30 minutes, then the phases are separated. The aqueous phase is extracted with 150+130 ml of toluene, the organic phase is concentrated and the residue is finally taken up with 200 ml of toluene. The toluene phases are collected, treated with 200 ml of deionized water and the pH is adjusted to 3.0 by addition of acetic acid The phases are separated and the organic one is extacted with a mixture of 120 ml of acetic acid and 190 ml of deionized water. The aqueous phase containing the diol in form of its salt is collected and, under stirring, 300 ml of toluene are added thereinto, then the pH of the mixture is brought to about 10 by addition of 30% aqueous ammonium hydroxide. The phases are separated, the organic one is collected and the aqueous phase is extracted with 2×60 ml of toluene. The collected toluene phases are washed with 3×60 ml of deionized water. The organic phase is concentrated under vacuum at about 50° C. and 27.2 g (75%) of O-triphenylmethyl-3-hydroxymethyl-4-[α-hydroxy-α-3-(dimethylamino)propyl-4-fluorobenzyl]benzaldoxime as a light yellow product with a purity (HPLC)=94.5% are obtained.

$^1$H-NMR (CDCl$_3$) δ ppm: 1.45÷1.75 (2m, 2H, CH$_2$—CN), 4.07 and 4.31 (2d, 2H, CH$_2$O), 6,92 (pseudo t, 2H, H in ortho to F), 7.20÷7.40 (m, 20H, arom), 8.22 (s, 1H, CH=CN).

(c) To a solution of 23.3 g (0.039 mole) of O-triphenylmethyl-3-hydroxymethyl-4-[α-hydroxy-α-3-dimethylamino)propyl-4-fluorobenzyl]benzaldoxime in 260 ml of dichloromethane, 25.5 ml of triethylamine are added. The mixture is cooled to 5° C. and a solution of 6 ml of methanesulfonyl chloride in 300 ml of dichloromethane are slowly (in 3 hours) added thereinto, by keeping the temperature at 5÷7° C. After a control by HPLC showing a content in diol lower than 2%, 230 ml of 0.1 N NaOH are added to the reaction mixture, by maintaining its temperature at 0÷5° C. The phases are separated, the organic phase is washed three times with a mixture of 200 ml of deionized water and 25 ml of a 20% solution of sodium chloride. The aqueous phase is discarded, the organic one is collected and concentrated under vacuum to a solid residue. Thus, 22.3 g (97%) of O-triphenylmethyl-1-[3-(dimethylamino)propyl]-1-(4-fluorophenyl)-1,3-dihydro-5-isobenzofurancarbaldoxime as a pale yellow product with purity (HPLC)=90.8%.

$^1$H-NMR (CDCl$_3$) δ ppm: 1.15÷1.55 (2m, 2H, CH$_2$—C—N), 2.15 (s, 6H, N(CH$_3$)$_2$), 2.15÷2.35 (m, 4H, CH$_2$—C—CH$_2$—N), 5.08 (2d, 2H, CH$_2$—O), 6.93 (pseudo t, 2H, H in ortho to F), 7.20÷7.50 (m, 20H, arom.), 8.23 (s, 1H, CH=N).

(d) A mixture of 640 ml of acetic anhydride and 220 ml of 98% formic acid is heated one hour at 110° C., then it is cooled to 60° C. and 17.6 g (0.03 mole) of O-triphenylmethyl-1-[3-(dimethylamino)propyl]-1-(4-fluorophenyl)-1,3-dihydro-5-isobenzofurancarbaldoxime are added thereinto. The obtained mixture is heated at 120° C. for 5 hours. After a HPLC control showing a conversion into citalopram of 88.2% (area), the mixture is concentrated under vacuum at 60° C. to an oil which is taken up with 170 ml of ethyl actate and 350 ml of deionized water (pH of about 4). The pH is adjusted to 2.1 by addition of about 10 ml of 10% HCl. The phases are separated, the aqueous one is extracted with 170 ml of ethyl acetate. The organic phases are discarded and the pH of the aqueous phase is brought to 8.5 by addition of about 45 ml of 10% aqueous ammonium hydroxide; 90 ml of toluene are added thereinto and the mixture is kept under sting for 2 hours. The phases are separated and the aqueous one is extracted with 3×100 ml of toluene. The toluene phases are collected and concentrated under vacuum at 50° C. to a solid residue which is taken up with 35 ml of dichloromethane and loaded on a SiO$_2$ column by eluting with a dichloromethane/methanol=9/1 mixture. By concentration of the eluate, 7.1 g (73%) of citalopram base with purity (HPLC)=98.2% is obtained.

(e) To a solution of 7.1 g of citalopram base in 35 ml of dichloromethane a solution of 7 g of sodium metabisulphite in 25 ml of deionized water is added. The pH of the mixture is brought to 6.0 by addition of 5% aqueous ammonium hydroxide, then the organic phase is discarded, the aqueous one is brought to pH=7.0 by addition of sodium bicarbonate and extacted with 2×10 ml of toluene. The organic extracts are concentrated under vacuum at 50° C. to give 6.9 g of citalopram base with purity (HPLC)=99.8% (area). These 6.9 g of citalopram base are dissolved in 30 ml of acetone and 48% HBr is added to the solution to a pH of 4÷5. The obtained solution is evaporated under vacuum at 45° C. and the residue is crystallized with acetone to give 5.6 g of citalopram hydrobromide with purity HPLC)=99.4% (area) and m.p. 185÷187° C.

$^1$H-NMR DMSO-d$_6$) δ ppm: 1.30÷1.60 (m, 2H, C—CH$_2$—C—N); 2.21 (t, 2H, CH$_2$—C—C—N); 2.66 (s, 6H, N(CH$_3$)$_2$); 3.01 (t, 2H, CH$_2$—N); 5.20 (2d, 2H, CH$_2$O); 7.18 (pseudo t, 2H, H in ortho to F); 7.55÷7.62 (dd, 2H, H in meta to F); 7.27÷7.83 (m, 3H, H arom., phthalide); 9.22 (br s, 1H, NH exchanged with D$_2$O).

What is claimed is:

1. A process for the preparation of 5-formylphthalide of formula

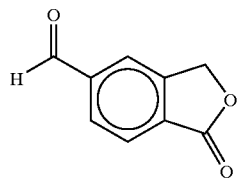

which comprises submitting a halide of formula

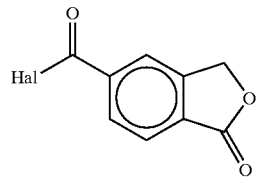

wherein Hal represents chlorine, bromine or iodine, dissolved in a dipolar aprotic solvent to hydrogenation, where the dipolar aprotic solvent is selected from the group consisting of N,N-dimethylformamide (DMF), N,N-dimeithylacetamicde (DMA), dimethylsulfoxide (DMSO) and acetonitrile, and where the hydrogenation is carried out in the presence of a hydrogenation catalyst selected from the group consisting of palladium on charcoal (Pd/C) and palladium on barium sulphate (Pd/BaSO$_2$).

2. The process of claim 1 wherein said dipolar aprotic solvent is N,N-dimethyl acetamide.

3. The process of claim 1 wherein said hydrogenation catalyst is used, compared to the halide of formula II in a weight/weight ratio comprised betwee 0.2:1 and 0.05:1.

4. The process of claim 1 wherein the halide of formula II is the chlorocarbonyl phthalide.

5. The process of claim 1 wherein the concentration of the halide of formula II is comprised between 60 and 80 g/l.

6. The process of claim 1 wherein the hydrogenation is carried out at a pressure between 1 and 5 bar.

7. The process of claim 1 wherein the hydrogenation is carried out at a temperature comprised between room remperantre and 120° C.

8. The process of claim 3 where said hydrogenation catalyst is used, compared to the halide of formula II in a weight/weight ratio of about 0.1:1.

9. The process of claim 5, wherein the concentration of the halide of formula II is about 70 g/l.

10. The process of claim 6 wherein the hydrogenation is carried out at a pressure between 2.5 and 3.5 bar.

* * * * *

Disclaimer

6,888,010 B2—Leone Dall'Asta, Milan (IT); Giovanni Cotticelli, Cernusco sul Naviglio (IT). PROCESS FOR THE PREPARATION OF 5-FORMYLPHTHALIDE. Patent dated May 3, 2005. Disclaimer filed February 10, 2012, by the inventors.

Hereby disclaims complete claims 1-10 of said patent.

(*Official Gazette, October 23, 2012*)